US010791990B2

(12) United States Patent
Goyal et al.

(10) Patent No.: US 10,791,990 B2
(45) Date of Patent: Oct. 6, 2020

(54) TISSUE DETECTION SYSTEM WITH A POLYMER NEEDLE

(71) Applicant: Regents of the University of Minnesota, Minneapolis, MN (US)

(72) Inventors: Amit Goyal, St. Anthony, MN (US); Michael A. Greminger, Duluth, MN (US); Brian J. Krohn, St. Paul, MN (US); Anastasia N. Zink, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 461 days.

(21) Appl. No.: 15/621,096

(22) Filed: Jun. 13, 2017

(65) Prior Publication Data

US 2017/0354379 A1 Dec. 14, 2017

Related U.S. Application Data

(60) Provisional application No. 62/349,557, filed on Jun. 13, 2016, provisional application No. 62/349,551, filed on Jun. 13, 2016.

(51) Int. Cl.
*A61B 5/00* (2006.01)
*A61B 5/06* (2006.01)
(Continued)

(52) U.S. Cl.
CPC ............ *A61B 5/6848* (2013.01); *A61B 5/061* (2013.01); *A61B 10/0045* (2013.01);
(Continued)

(58) Field of Classification Search
CPC ............ A61B 10/0045; A61B 17/3401; A61B 17/3403; A61B 2010/0077;
(Continued)

(56) References Cited

U.S. PATENT DOCUMENTS 2,763,935 A 9/1956 Whaley
4,224,949 A 9/1980 Scott et al.
(Continued)

FOREIGN PATENT DOCUMENTS

DE 4420232 A1 12/1995
EP 2787893 B1 2/2017
(Continued)

OTHER PUBLICATIONS

"Allegro™ Single-Use Filling Needles Datasheet", [online]. © 2013, Pall Corporation. [archived on Nov. 23, 2015]. Retrieved from the Internet: <URL: http://web.archive.org/web/20151123034936/www.pall.com/pdfs/Biopharmaceuticals/USD2836-Allegro-Single-use-Filling-Needles-Datasheet-Nov-2013.pdf>, (2013), 4 pgs.
(Continued)

*Primary Examiner* — Christine H Matthews
(74) *Attorney, Agent, or Firm* — Schwegman Lundberg & Woessner, P.A.

(57) ABSTRACT

A detection system can include a device, a circuit, and at least one indicator. The device can include polymer needle having a distal end and a proximal end. A needle lumen can be extended along a longitudinal axis of the polymer needle. The distal end can include an insertion tip. An elongate sleeve can include a first end and a second end. The polymer needle can be located within an inner bore of the elongate sleeve. The insertion tip of the polymer needle can be disposed at a distance from the elongate sleeve. A first electrode can be coupled to the device and a second electrode can be electrically isolated from the first electrode. The circuit can be configured to provide a signal based on an electrical characteristic between the first electrode and the second electrode. At least one indicator can be communicatively coupled to the circuit and configured to provide an output based on the signal.

26 Claims, 7 Drawing Sheets

(51) Int. Cl.
*A61B 10/00* (2006.01)
*A61B 17/34* (2006.01)
*A61B 90/00* (2016.01)
*A61B 17/00* (2006.01)

(52) U.S. Cl.
CPC .......... *A61B 17/3401* (2013.01); *A61B 5/489* (2013.01); *A61B 5/4893* (2013.01); *A61B 5/4896* (2013.01); *A61B 17/3403* (2013.01); *A61B 2010/0077* (2013.01); *A61B 2017/00026* (2013.01); *A61B 2090/062* (2016.02); *A61B 2090/0807* (2016.02)

(58) Field of Classification Search
CPC .... A61B 2017/00026; A61B 2090/062; A61B 2090/0807; A61B 5/061; A61B 5/4896; A61B 5/6848
See application file for complete search history.

(56) References Cited

U.S. PATENT DOCUMENTS

| | | | |
|---|---|---|---|
| 5,271,413 | A | 12/1993 | Dalamagas et al. |
| 6,015,398 | A | 1/2000 | Arimatsu et al. |
| 6,709,380 | B2 | 3/2004 | Green |
| 6,760,616 | B2 | 7/2004 | Hoey et al. |
| 7,050,848 | B2 | 5/2006 | Hoey et al. |
| 8,090,436 | B2 | 1/2012 | Hoey et al. |
| 8,419,746 | B2 | 4/2013 | Bourlion et al. |
| 9,949,652 | B2 * | 4/2018 | Fischell .............. A61B 5/04001 |
| 2002/0102185 | A1 | 8/2002 | Tatsumi |
| 2004/0010204 | A1 | 1/2004 | Weber et al. |
| 2004/0158136 | A1 * | 8/2004 | Gough ................ A61B 5/14546 600/328 |
| 2006/0224078 | A1 | 10/2006 | Hoey |
| 2009/0036794 | A1 | 2/2009 | Stubhaug et al. |
| 2011/0160731 | A1 * | 6/2011 | Bleich ................ A61B 17/1671 606/79 |
| 2012/0004625 | A1 | 1/2012 | Velez-Rivera |
| 2014/0012226 | A1 | 1/2014 | Hochman |
| 2015/0230724 | A1 | 8/2015 | Waziri et al. |
| 2015/0342635 | A1 | 12/2015 | Tsamir |
| 2019/0150840 | A1 | 5/2019 | Darrow et al. |

FOREIGN PATENT DOCUMENTS

| | | |
|---|---|---|
| WO | WO-2009019707 A1 | 2/2009 |
| WO | WO-2012099984 A1 | 7/2012 |

OTHER PUBLICATIONS

"American Society of Anesthesiologists—Residency Information by State", [online]. [archived on Apr. 26, 2016]. Retrieved from the Internet: <URL: https://web.archive.org/web/20160426121615/http://www.asahq.org/about-asa/component-societies/asa-resident-component/residency-information-by-state>, (2016), 6 pgs.

"GlobalData Medical Devices and Equipment", [online]. [archived on Apr. 3, 2016]. Retrieved from the Internet: <URL: https://web.archive.org/web/20160403211444/http://medical.globaldata.com:80/>, (2016), 2 pgs.

Balki, M., et al., "Ultrasound Imaging of the Lumbar Spine in the Transverse Plane: The Correlation Between Estimated and Actual Depth to the Epidural Space in Obese Parturients", Anesth. Analg.,108(6), (Jun. 2009), 1876-1681.

Baumann, S. B., et al., "The Electrical Conductivity of Human Cerebrospinal Fluid at Body Temperature", IEEE Transactions on Biomedical Engineering, 44(3), (Mar. 1997), 220-223.

Borsic, A. R., et al., "Sensitivity Study and Optimization of a 3D Electric Impedance Tomography Prostate Probe", Physiological Measurement, 30(6), (2009), S1-S18.

Fisher, S. C., et al., "Is obesity still increasing among pregnant women? Prepregnancy obesity trends in 20 states, 2003-2009", Preventive Medicine, 56(6), (2013), 372-378.

Gabriel, Sami, et al., "The Dielectric Properties of Biological Tissues: III. Parametric Models for the Dielectric Spectrum of Tissues", Physics in Medicine and Biology, 41(11), (1996), 2271-2293.

Gradert, T. L., et al., "Safety of Chronic Intrathecal Morphine Infusion in a Sheep Model", Anesthesiology, 99(1), (2003), 188-198.

Harrington, B. E., et al., "Meningeal (postdural) puncture headache, unintentional dural puncture, and the epidural blood patch: a national survey of United States practice", Reg. Anesth. Pain Med., 34(5), (2009), 430-437, (2009), 2 pgs.

Kalvoy, Havard, et al., "Impedance-based tissue discrimination for needle guidance", Physical Meas., 30(2), (2009), 129-140.

Konrad, C., et al., "Learning Manual Skills in Anesthesiology: Is There a Recommended Number of Cases for Anesthetic Procedures?", Anesth. Analg., 86(3), (1998), 635-639.

Pal, Anirban, et al., "Do Pencil-Point Spinal Needles Decrease the Incidence of Postdural Puncture Headache in Reality? A Comparative Study between Pencil-Point 25G Whitacre and Cutting-Beveled 25G Quincke Spinal Needles in 320 Obstetric Patients", Anesthesia, Essays and Researches 5(2), 162-166, (2011), 9 pgs.

Parker, R. K., et al., "A Microscopic Analysis of Cut-Bevel versus Pencil-Point Spinal Needles", Anesthesia and Analgesia 85(5), (1997), 1101-1104.

Rosero, E. B., et al., "Nationwide incidence of serious complications of epidural analgesia in the United States", Acta Anaesthesiologica Scandinavica, (Feb. 2016), 1-11.

Satpathy, H. K., et al., "Labor and Delivery, Analgesia, Regional and Local", Medscape Reference, (Nov. 13, 2015), 20 pg.

Serpell, M. G., et al., "Pencil Point Spinal Needles and Neurological Damage", British Journal of Anaesthesia 89(5), (2002), 800-801.

Tran, De Q. H., et al., "Confirmation of Loss-of-Resistance for Epidural Analgesia", Reg. Anesth. Pain Med., 40(2), (2015), 166-173.

Turnbull, D. K., et al., "Post-dural puncture headache: pathogenesis, prevention and treatment", British Journal of Anaesthesia, 91(5), (Nov. 2003), 718-729.

Wan, Yuqing, et al., "Incorporating a Biopsy Needle as an Electrode in Transrectal Impedance Imagiing", 34th Annual International Conference of the IEEE EMBS San Diego, California USA, Aug. 28-Sep. 1, 2012, (2012), 6220-6223.

Webb, C. A.-J., et al., "Unintentional Dural Puncture with a Tuohy Needle Increases Risk of Chronic Headache", Anesth. Analg., 115(1), (Jul. 2012), 124-132.

* cited by examiner

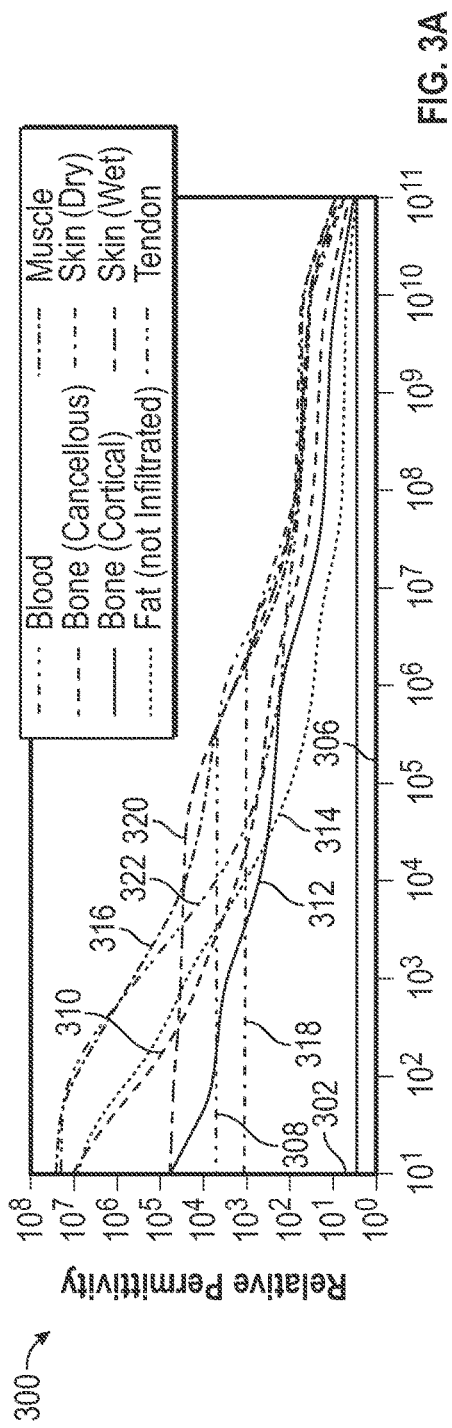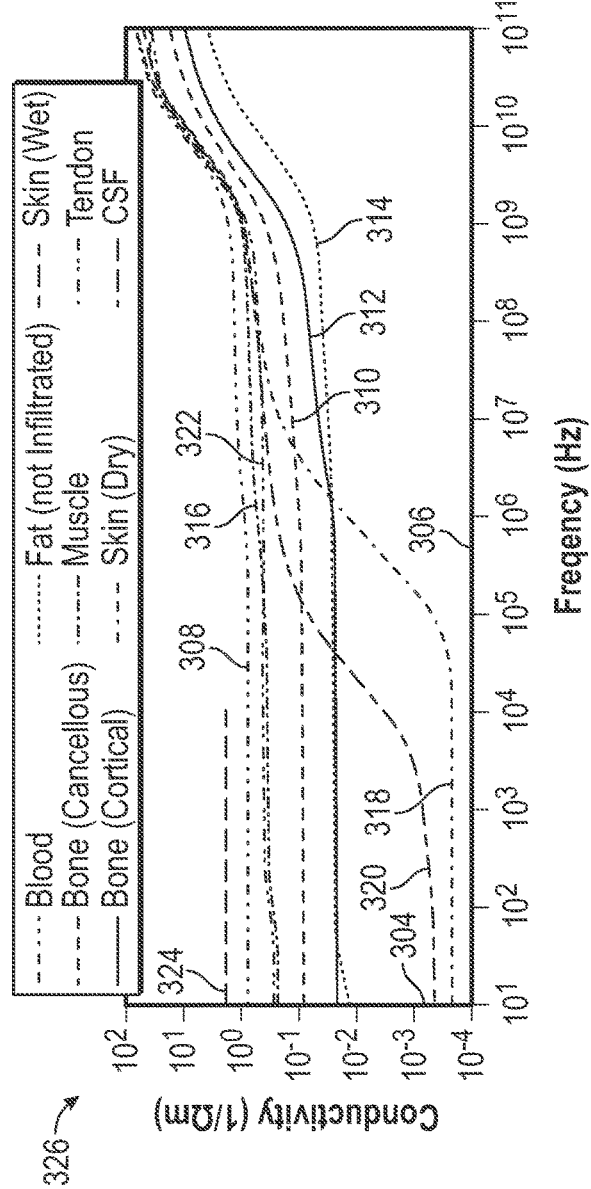
FIG. 3A
FIG. 3B

TISSUE DETECTION SYSTEM WITH A POLYMER NEEDLE

CLAIM OF PRIORITY

This patent application claims the benefit of priority of U.S. Provisional Patent Application Ser. No. 62/349,557, entitled "TISSUE DETECTION SYSTEM," filed on Jun. 13, 2016 and Patent Application Ser. No. 62/349,551, entitled "POLYMER NEEDLE WITH ENHANCED TACTILE FEEDBACK," filed on Jun. 13, 2016, the benefit of priority of each of which is claimed hereby, and each of which are incorporated by reference herein in its entirety.

BACKGROUND

Needles, such as lumbar puncture needles, can be used in the medical, diagnostics, and biological research fields for retrieving samples, injecting tissue, or transporting fluids. Some needles are used to access the epidural space or subarachnoid space of a patient for the delivery of anesthesia, obtaining fluid samples, or obtaining tissue samples. Such needles can include a hollow shaft with a beveled tip at an insertion end. The beveled tip can cut tissue in the process of insertion into a patient or a sample due to the beveled geometry at the tip. Atraumatic needles have been developed, which can cause less tissue damage than beveled tip needles. However, the user of atraumatic needles may feel less tactile feedback while inserting the needle. Needles are often constructed from stainless steel because stainless steel has good biocompatibility and can be easily sterilized.

Traumatic lumbar punctures can occur in 20-30% of insertions. The likelihood of a traumatic lumbar puncture can be increased when the dural sac is not located on the first insertion. Accordingly, repeated insertions and withdrawals of the needle to locate cerebral spinal fluid (CSF) within the dural sac can lead to a higher likelihood of a traumatic lumber puncture. It can be difficult for a user to know when the needle tip is located at the desired location within the patient, for instance, within the dural sac. Insertion is often guided only by tactile feedback sensed by a person handling the needle.

SUMMARY

A polymer needle can reduce trauma to a patient and provide tactile feedback to a person handling the polymer needle during insertion. The polymer needle can include a distal end and a proximal end. A lumen can be extended along a longitudinal axis of the polymer needle to communicate fluid through the polymer needle. The distal end can include an insertion tip. An elongate sleeve can include a first end and a second end. The polymer needle can be located within an inner bore of the elongate sleeve. In some examples, the elongate sleeve can support the polymer needle. The insertion tip of the polymer needle can be disposed at a distance from the elongate sleeve.

In some examples, the polymer needle can be used independently or can be combined with a detection system. The detection system can include a circuit and at least one indicator. The polymer needle can include at least one electrode. A first electrode can be coupled to the polymer needle and a second electrode can be electrically isolated from the first electrode. The circuit can be configured to provide a signal based on an electrical characteristic between the first electrode and the second electrode. At least one indicator can be communicatively coupled to the circuit and configured to provide an output based on the signal.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3A-B are examples of charts illustrating electrical characteristics of various tissues, according to an embodiment.

DETAILED DESCRIPTION

Figure 1:
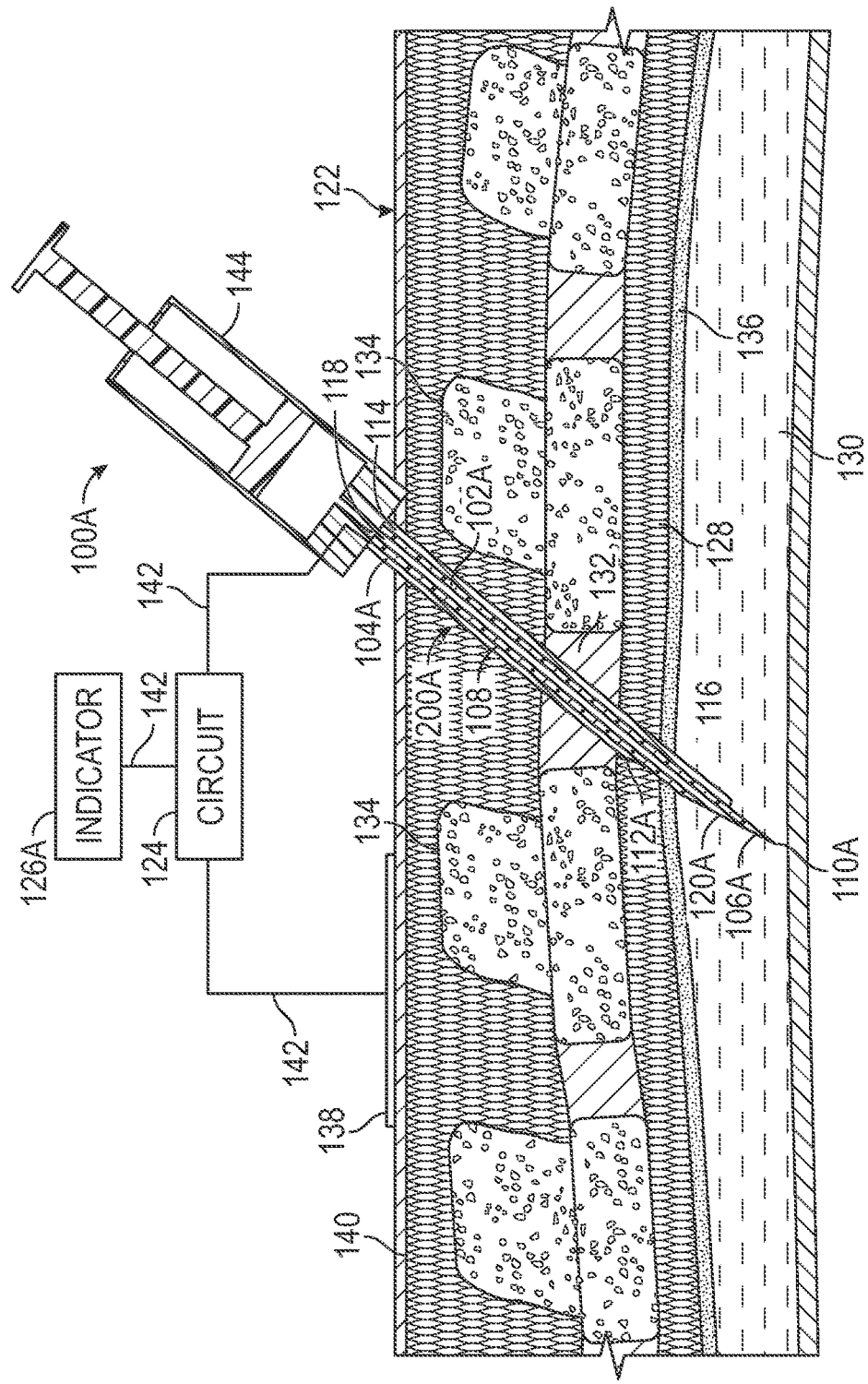
FIG. 1 is a partial cross section of an example of a tissue detection system including a polymer needle located in a lumbar region of a patient, according to an embodiment.

The present application relates to devices and techniques for a device, such as a polymer needle for atraumatic lumbar punctures or a polymer needle combined with a detection system, such as a detection system configured for indicating a location of a distal end of a device within a lumbar region of a patient. The following detailed description and examples are illustrative of the subject matter disclosed herein; however, the subject matter disclosed is not limited to the following description and examples provided. Portions and features of some embodiments may be included in, or substituted for, those of other embodiments. Embodiments set forth in the claims encompass all available equivalents of those claims.

The present inventors have recognized, among other things, that reducing trauma to a patient from a needle injection, such as a lumbar puncture, can reduce the risk of blood contamination. Reducing trauma from the needle injection can also reduce temporary or permanent nerve damage, blood clotting, blood vessel damage, or tissue damage surrounding a nerve or blood vessel. Needle tips constructed from stainless steel, including stainless steel needles having a beveled tip, can cut or core tissue during penetration of the body of the patient.

The present inventors have also recognized, among other things, that reducing blood contamination of a cerebral spinal fluid (CSF) sample resulting from a traumatic insertion of the needle into the dural sac (i.e., arachnoid) can increase the accuracy of some diagnostic tests. For instance, blood contamination within the CSF can confound a diagnosis of subarachnoid hemorrhage, which can be diagnosed by measuring the amount of blood in the CSF. Reducing trauma to a patient from a needle injection, such as a lumbar puncture, can reduce the risk of blood contamination.

The present subject matter can provide a solution to this problem, such as by providing a device having a polymer needle for reducing trauma to the tissue. For example, the polymer needle can reduce trauma to the patient by reducing friction between the polymer needle and the tissue of the patient. The polymer needle can include a distal end and a proximal end. A needle lumen can extend along a longitudinal axis of the polymer needle. An elongate sleeve can include a first end and a second end. The polymer needle can be located within an inner bore of the elongate sleeve. Accordingly, the elongate sleeve can support the polymer needle to increase the stiffness of the device for insertion. An insertion tip of the polymer needle can be disposed at a distance from the elongate sleeve. For instance, the polymer needle can be disposed at a distance from the first end of the elongate sleeve. In other examples, the insertion tip of the polymer needle can be flush with the first end. When the insertion tip is extended from the first end of the elongate sleeve, the insertion tip (fabricated from a low friction polymer) contacts the tissue first, separating rather than cutting the tissue.

The present inventors have also recognized, among other things, that increasing the tactile feedback to a user inserting the needle into the patient can reduce trauma to the patient related to contact with the spinal cord or other nerve, such as improper or unintended placement of the needle. In some instances, tactile feedback is the primary method for guiding the needle to an intended location within the body of the patient. Increasing the tactile feedback produced by the needle can increase the accuracy of the needle placement.

The present subject matter can provide a solution to this problem, such as by providing a device having a polymer needle for reducing trauma to the tissue and having increased tactile feedback for improving the user's perception of the placement of the device. For instance, the insertion tip can include a beveled surface to provide tactile feedback to a person handling the device during insertion. In some examples, the elongate sleeve can include a dull transition between an outer dimension and the inner bore. In an example, the dull transition can provide tactile feedback.

The present inventors have recognized, among other things, that determining a location of a needle within the lumbar region of a patient for diagnostic or therapeutic purposes can reduce trauma to the patient or reduce potential for error in the treatment or diagnosis of the patient. For instance, a lumbar puncture can be used to diagnose conditions, such as meningitis, normal pressure hydrocephalus, or subarachnoid hemorrhage. For a lumbar puncture, the needle must penetrate the dural sac in order to take a sample of CSF. For instance, the needle can be inserted through the ligamentum flavum, through the epidural space, and through the arachnoid to reach the subarachnoid space. For anesthesia administration, the needle can be inserted into the epidural space or the subarachnoid space, depending upon the treatment. Epidural anesthesia is often administered during childbirth and requires that the anesthesia be delivered to the epidural space. The epidural space is located between the ligamentum flavum and the dural sac. For epidural anesthesia, an aperture of the needle must be located between the ligamentum flavum and the dural sac for delivery of anesthesia to the epidural space. Determining the location of the needle can be difficult. Tactile feedback from the needle is the primary method for guiding the needle to an intended location within the body of the patient. During child birth, the use of fluoroscopy to determine the location of the needle is not an option due to a risk of radiation to the fetus.

The present inventors have also recognized, among other things, that determining the location of the needle within the lumbar region of a patient can reduce trauma to the patient related to contact with the filum terminale, spinal cord, or other nerve, resulting from improper or unintended placement of the needle. For instance, being able to identify the location of the needle within the patient can reduce the need for multiple insertions. The ability to accurately and precisely determine the location of the needle can also increase the effectiveness of delivering treatment to the patient or providing a diagnosis.

The present subject matter can provide a solution to this problem, such as by providing a detection system for determining the location of an insertion tip of a needle within a patient, such as the insertion tip of the polymer needle. The detection system can include a device, a circuit, and at least one indicator. A first electrode can be coupled to the device and a second electrode can be electrically isolated from the first electrode. The circuit can be configured to provide a signal based on an electrical characteristic between the first electrode and the second electrode. For instance, the circuit can provide a signal based on an impedance of tissue located relative to the first electrode and the second electrode. In an example, the impedance or other electrical characteristic can be correlated to a tissue type. At least one indicator can be communicatively coupled to the circuit and configured to provide an output based on the signal. Accordingly, the detection system can indicate a location of the insertion tip within the lumber region.

FIG. 1 depicts an example of a partial cross section of a detection system 100A including a device 200A inserted into a lumbar region of a patient. The detection system 100A can include the device 200A, a circuit 124 (depicted in schematic form for the sake of illustration), and indicator 126A (also depicted in schematic form). The device 200A can include a polymer needle 102A located within an inner bore 108 of an elongate sleeve 104A. The elongate sleeve can include a first end 112A and a second end 114. The polymer needle 102A can include a distal end 106A and a proximal end 118. The first end 112A can be located closer to the distal end 106A than the second end 114. An insertion tip 110A can be located at an apex of the distal end 106A.

The device 200A can include a first electrode coupled to the polymer needle 102A, and a second electrode can be electrically isolated from the first electrode. For instance, in the example of FIG. 1, the first electrode can be the elongate sleeve 104A and the second electrode can be an electrode pad 138. The electrode pad 138 can be located on skin 140 near a needle insertion location. The first electrode and the second electrode can be constructed from an electrically conductive and biocompatible material including, but not limited to, stainless steel, titanium, or other electrically conductive and biocompatible material.

The device 200A can be inserted into a patient, such as in a lumbar region 122 of a patient. The lumbar region 122 can include an epidural space 128 and a subarachnoid space 130.

The distal end 106A of the polymer needle 102A can be inserted into the epidural space 128 or the subarachnoid space 130 for the purpose of diagnosis or treatment. To reach the epidural space 128, the distal end 106A must be inserted through a ligamentum flavum 132 located between two vertebrae 134. The epidural space 128 includes fatty tissue. To reach the subarachnoid space 130, the distal end 106A can be inserted further into the patient and through the arachnoid 136 of the dural sac. The subarachnoid space within the dural sac includes CSF.

The circuit 124 can be electrically coupled to the first electrode and the second electrode. For instance, the circuit 124 can be connected to the first electrode or the second electrode by at least one wire 142 or wirelessly using a radio transceiver. The circuit 124 can provide a signal based on an electrical characteristic between the first electrode and the second electrode. In one example, the electrical characteristic can be an electrical impedance between the first electrode and the second electrode. In a further example, the signal can be provided based on the electrical characteristic being within a target range. For instance, the electrical characteristic can correspond to various tissue types, such as ligament, fat, CSF, or other tissue. A chart showing various electrical characteristics for some tissues is shown in FIG. 3. For example, an electrical characteristic of fat can be different than an electrical characteristic of CSF. The signal can be provided based on the electrical characteristic being within the target range corresponding to the respective tissue types. Accordingly, the circuit can be configured to provide a signal that communicates whether the first end 112A is located within the ligamentum flavum 132, the epidural space 128, the subarachnoid space 130, or other tissue or fluid.

Figure 4:
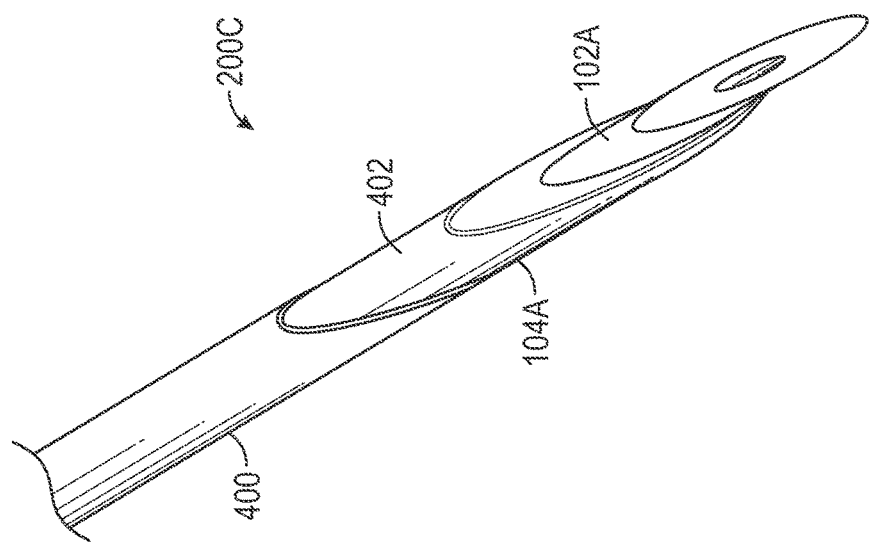
FIG. 4 is a perspective view of a device including an insulated cover, according to an embodiment.

In the example of FIG. 1, where the elongate sleeve 104A is the first electrode and the electrode pad 138 is the second electrode, the output can communicate that at least the first electrode is in contact with ligament, blood, bone, fat, or other tissue. For instance, the circuit 124 can provide the signal based on a combined electrical characteristic of a plurality of tissues located between the first end 112A and the electrode pad 138. In an example, the combined electrical characteristic can be dominated by the electrical characteristic of the tissue located at the first end 112A. For instance, where the electrical characteristic is based on resistance or impedance, the electrical characteristic will be dominated by the tissue in contact with the first or second electrode having the smaller surface area in contact with the tissue. In an example, the first electrode can be the first end 112A. The first end 112A can be electrically isolated from the remaining portion of the elongate sleeve 104A. In an example, the elongate sleeve 104A can be electrically isolated from the tissue along the length of the elongate sleeve with the exception of the first end 112A. For instance, the elongate sleeve can include an insulated covering as shown in FIG. 4 and described further herein. The first end 112A can include a smaller surface area than the electrode pad 138. Accordingly, the electrical characteristic in contact with the first end 112A can dominate the combined electrical characteristic.

The circuit 124 can be hardware or software implemented. For instance, the circuit 124 can include one or more hardware components electrically coupled in a circuit. In some examples, the hardware components can include, but are not limited to, resistors, capacitors, diodes, or transistors. The hardware components can be configured to provide the signal based on the electrical characteristics. For example, the hardware components can be arranged in an electrical circuit to provide the signal where the electrical characteristics are within the target range. In further examples, the circuit 124 can include software components. For instance, the hardware can include a processor and memory having instructions stored thereon to provide the signal based on the electrical characteristic. In one example, the detection system 100A can include a module having the hardware and software components. In other examples, the detection system 100A can include the hardware components, and the software components can be stored on a computer that can be communicatively coupled to the detection system 100A. For instance, the computer can be electrically coupled by wires, fiber optic cable, or wirelessly coupled.

The indicator 126A can be communicatively coupled to the circuit 124. For instance, the indicator 126A can be electrically coupled by one or more wires 142 or wirelessly. The indicator 126A can be configured to provide an output based on the signal. For instance, where the signal is based on an electrical characteristic corresponding to CSF, the indicator 126A can provide the output communicating to the user that at least the first electrode is in contact with CSF. In an example, the indicator 126A can provide the output communicating to the user that the first electrode and the second electrode are in contact with CSF. In the example of FIG. 1, where the elongate sleeve 104A is the first electrode and the electrode pad 138 is the second electrode, the output can communicate that at least the first electrode is in contact with ligament, blood, bone, fat, or other tissue. For instance, the output can communicate that the first end 112A is in contact with ligament, blood, bone, fat, or other tissue. In various examples, the indicator 126A can include a display, light, speaker, vibration motor, piezoelectric transducer, or other indicator. For instance, the output can include a message, text, or symbol on the display; illumination of the light; a sound from the speaker, generation of a vibration, or other output.

In an example the circuit 124 can provide more than one signal based on more than one respective electrical characteristics. The indicator 126A can provide more than one output corresponding to the more than one respective signal. For instance, a plurality of indicator 126A can provide a plurality of respective outputs based on a plurality of signals. In one example, the circuit 124 can provide a unique signal for ligament, fat, and CSF respectively. Accordingly, the indicator 126A can provide a unique output for each signal based on the ligament, fat, and CSF respectively. In other examples, the circuit 124 can also provide a unique signal for blood, bone, or other tissues. The plurality of indicators 126A can provide respective output corresponding to the unique signal for blood, bone, or other tissues.

As shown in the example of FIG. 1, the polymer needle 102A can be fluidly coupled to an apparatus 144 for administering a therapeutic treatment or extracting a fluid or a tissue sample from the patient for diagnostic purposes. The apparatus 144 can include a syringe, a catheter, or the like. In the example of FIG. 1, the polymer needle 102A can include a lumen 116, also referred to as a needle lumen. The lumen 116 can terminate at an aperture 120A located at the distal end 106A. For instance, the aperture 120A can be located on a surface of the distal end 106A. The surface of the distal end 106A can include, for example, a beveled surface, curved surface, arcuate surface, or side surface of the polymer needle 102A. The lumen 116 can be configured to communicate fluid or tissue. For instance, the lumen 116 can fluidly couple the aperture 120A to the apparatus 144. The lumen 116 can be fluidly coupled to a reservoir of the apparatus 144. The elongate sleeve 104A can be fastened to the apparatus 144 by threads, press fitting, ultrasonic welding, adhesive, or other method. In an example, the polymer needle 102A can be sealed to the apparatus 144 for communication of fluids or tissue samples between the device 200A and the apparatus 144.

Figure 2:
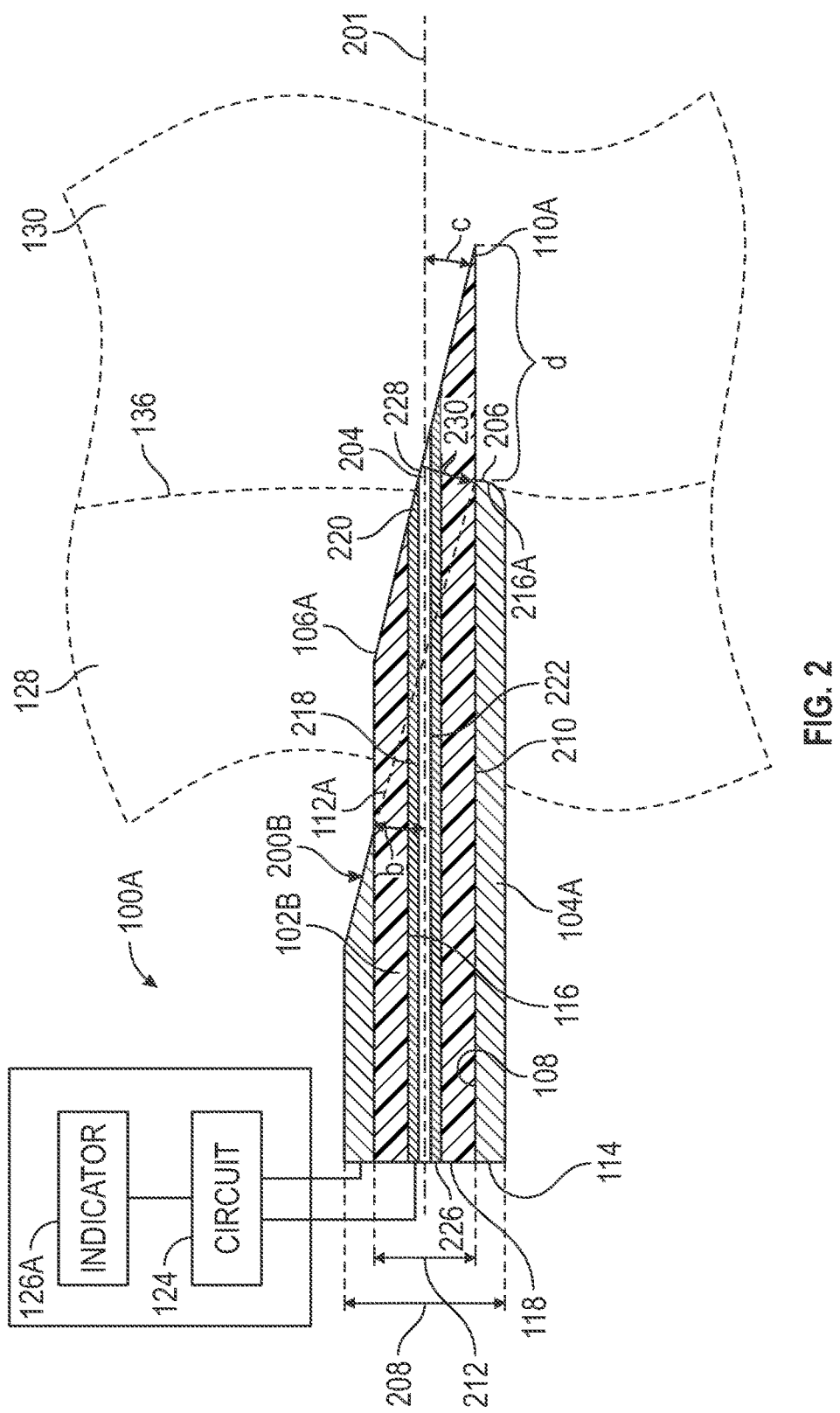
FIG. 2 shows a cross section of a tissue detection system including a polymer needle, according to an embodiment.

FIG. 2 shows a cross section of an example of a device 200B. The cross section is cut at a location along a longitudinal axis 201. In the example of FIG. 2, a detailed partial view of the device 200B is shown to better illustrate the detail of the device 200B. Accordingly, the entire length of the device 200B is not illustrated or drawn to scale. A polymer needle 102B can include the distal end 106A and the proximal end 118. An outer surface of the polymer needle 102B can include, but is not limited to, a circular, rectangular, triangular, oval, or other cross sectional shape along the longitudinal axis 201 of the polymer needle 102B. The polymer needle 102B can include an outer dimension 212 also referred to as an outer needle dimension. Where the polymer needle 102B includes a circular cross sectional shape, the polymer needle 102B can include an outer diameter, also referred to as an outer needle diameter. In the example of FIGS. 1 and 2, the distal end 106A can include a beveled configuration. For instance, the distal end 106A can include the beveled surface. The beveled surface of the distal end 106A can be aligned at an acute angle c with respect to the longitudinal axis 201. The acute angle c can include, but is not limited to an angle between 10 degrees and 45 degrees. Accordingly, the tactile feedback characteristics of the polymer needle 102B can be increased as compared to needles having conical shaped tips, such as conical shaped tips with an acute angle less than 10 degrees with respect to the longitudinal axis 201.

In an example, the material of the polymer needle 102B can have a low coefficient of friction, such as a low static coefficient of friction. The low static coefficient of friction can reduce tearing or cutting of the tissue during insertion of the polymer needle 102B as compared to a stainless steel needle having the same shape and dimensions. For instance, the polymer needle 102B can have a static coefficient of friction between 0.55 and 0.05. The static coefficient of friction can be measured using ASTM D1894 or ASTM D3702. When in contact with stainless steel, for example, a polymer needle fabricated of polyether ether ketone (PEEK) can have a static coefficient of friction of about 0.20 when tested per ASTM D3702 and a similar static coefficient of friction when tested per ASTM D1894. In an example, PEEK can have a lower static coefficient of friction than stainless steel depending upon the material that PEEK is in contact with. When measuring the static coefficient of friction for a stainless steel sample in contact with another stainless steel sample, the static coefficient of friction can be between of 0.70 and 0.80 when tested per ASTM D1894. The low static coefficient of friction of the distal end 106A can reduce an amount of cutting or tearing of the tissue by instead separating the tissue during insertion. Accordingly, the polymer needle 102B can mitigate tissue damage associated with insertion of the device 200B.

The elongate sleeve 104A can include the first end 112A and the second end 114, as previously discussed. An outer dimension 208 of the elongate sleeve 104A can include, but is not limited to, a dimension between 0.20 mm to 4.5 mm. In the example of FIG. 2, the outer dimension can be 1.27 mm. The outer dimension 208 can also be referred to as a sleeve diameter. The polymer needle 102B can be located within the inner bore 108 of the elongate sleeve 104A. In an example, the elongate sleeve 104A can be fixedly attached to the polymer needle 102B. For instance, an adhesive (e.g., epoxy) can be located between the elongate sleeve 104A and the polymer needle 102B, or the polymer needle 102B can be press-fit within the inner bore 108. In other examples, the polymer needle 102B can be removably coupled to the elongate sleeve 104A. For instance, the polymer needle 102B can be removed from the elongate sleeve 104A for sterilization.

The elongate sleeve 104A can support the polymer needle 102B between the first end 112A and the second end 114. For instance, the elongate sleeve 104A can reinforce the polymer needle 102B located within the inner bore 108 to reduce bending or increase the rigidity of the polymer needle 102B. Accordingly, an overall dimension, e.g., the outer dimension 208 in the example of FIG. 2, can be reduced as compared to a polymer needle 102B without the elongate sleeve 104A. In an example, a material of the elongate sleeve 104A can include a higher elastic modulus than a material of the polymer needle 102B. The polymer needle 102B can be constructed from a material including, but not limited to, PEEK, polytetrafluaroethlene (PTFE), polyethersulfone (PES), polysulfone (PS), polypropylene (PP), or other polymer. The elongate sleeve 104A can be constructed from a material having a higher stiffness than the material of the polymer needle 102, such as a material including, but not limited to, stainless steel, titanium, or other biocompatible metals. In one example, the elongate sleeve 104A can be located along the outer dimension 212 to support the polymer needle 102B. For instance, the polymer needle 102B can be located within the elongate sleeve 104A.

The material of the polymer needle 102B and the elongate sleeve 104A can be biocompatible. For instance, the material of the polymer needle 102B and the material of the elongate sleeve 104A can be chemically resistant to bodily fluids and other fluids or substances used in life sciences, such as cleaning products, injectable fluids, or the like. Accordingly, the device 200B can be suitable for insertion into a patient, into tissue samples, or the like.

As shown in the example of FIG. 2, the first end 112A of the elongate sleeve 104A can be beveled. For instance, the first end 112A can be aligned at the acute angle b. The first end 112A can be parallel with the beveled surface of the distal end 106A. In a further example, the first end 112A can be aligned at any angle b between 10 degrees and 45 degrees independently of the acute angle of the distal end 106A. For instance, the angle b of the first end 112A can be different than the angle c of the distal end 106A of the polymer needle 102B.

In an example, the first end 112A can be oriented normal to the longitudinal axis 201. In the example of FIG. 2, the first end 112A can include a dull transition 216A between an outer dimension 208 and the inner bore 108. In other words, the first end 112A can include the dull transition 216A between the elongate sleeve 104A and the polymer needle 102B. The dull transition 216A is adapted to reduce tissue damage caused by the first end 112A. The dull transition 216A can include, but is not limited to a chamfer or a fillet. In the example of FIG. 2, the dull transition 216A is a fillet.

The device 200B can include a stylet 218. The stylet 218 can be located within the needle lumen 116. In an example, the stylet 218 can include a proximal stylet end 226 and a distal stylet end 220. As shown in FIG. 2, the distal stylet end 220 can be substantially aligned with the distal end 106A, such as the beveled surface. In other examples, the distal stylet end 220 can be located 1.0 mm or less from the surface of the distal end 106A.

In a further example, the stylet 218 can include a stylet lumen 222 located between the distal stylet end 220 and the proximal stylet end 226. In one example, an adhesive can be disposed between the lumen 116 and the stylet 218 to fixedly couple the stylet 218 within the lumen 116. In a further example, the stylet 218 can be ultrasonically welded or press fit into the lumen 116. The stylet lumen 222 can terminate at an aperture 204, also referred to as a stylet aperture.

The insertion tip 110A is disposed at a distance d from a first end 112A of the elongate sleeve 104A. For instance, the distal end 106A protrudes from the first end 112A of the elongate sleeve 104A. In various examples, the distance d can be, but is not limited to, a dimension of between 0.1 mm to 10.0 mm. In the example of FIG. 1, the distal end 106A can include the beveled surface. Accordingly, the distal end 106A is configured to contact the tissue before the first end 112A during insertion into a patient, tissue sample, or the like. In an example, the distance d can be correlated to the outer dimension 208. For instance, the insertion tip 110A can be disposed from the first end 112A according to a ratio of the distance d to the outer dimension 208 or the ratio of the distance d to the outer dimension 212. In an example, the ratio can be in a range between 0.02 to 50.

In various examples, the stylet 218 can be the first electrode and the electrode pad 138 can be the second electrode, or the stylet 218 can be the first electrode and the elongate sleeve 104A can be the second electrode. In the example of FIG. 2, the elongate sleeve 104A can be the first electrode and the stylet 218 can be the second electrode. The polymer needle 102B can be an electrical isolator between the stylet 218 and the elongate sleeve 104A. The polymer needle 102B can be constructed from a dielectric material, for instance, the material of the polymer needle 102A can include, but is not limited to the materials of the polymer needle 102B previously discussed herein. An electrical path 230, such as a path of least electrical impedance or electrical resistance, can be located between the first electrode and the second electrode. In an example, the elongate sleeve 104A can be aligned with the aperture 204. For instance, the distal stylet end 220 and the first end 112A can be aligned so a length of the electrical path 230 is reduced. In a further example, the distal stylet end 220 can be aligned with the first end 112A so the aperture 204 is located distally from the first end 112A. In the example of FIG. 2, the elongate sleeve 104A can include a leading point 206 located at an apex of the first end 112A. The leading point 206 can be located at the distance d from the insertion tip 110A. The distance d can be adjusted to align the leading point 206 laterally from a center 228 of the aperture 204. Accordingly, the circuit 124 can provide the signal when the aperture 204 is located within a target tissue, such as ligament, bone, fat, CSF, or other tissue. For instance, in the example of FIG. 2, the polymer needle 102A is extended through the epidural space 128. The insertion tip 110A is penetrated through the arachnoid 136, and the aperture 204 is located within the subarachnoid space 130. Accordingly, the electrical path 230 is located within CSF located in the subarachnoid space 130. The circuit 124 (as shown in FIG. 1) can provide the signal based on the electrical characteristic of CSF to the indicator 126A. The indicator 126A can then provide an output corresponding to CSF.

FIGS. 3A-B illustrate charts 300 and 326 showing an example of electrical characteristics. For instance, the chart 300 shows a relative permittivity (along the Y-axis 302) and the chart 326 shows a conductivity (along the Y-axis 304) of various tissues and bodily fluids depending on frequency (along the X-axis 306 of charts 300 and 326). In the example of FIGS. 3A-B, the charts 300, 326 show electrical characteristics for blood 308, cancellous bone 310, cortical bone 312, infiltrated fat 314, muscle 316, dry skin 318, wet skin 320, tendon 322, and CSF 324. As previously discussed the circuit 124 can be configured to provide a signal based on the electrical characteristic of the tissue or fluid. Accordingly, the detection system 100A can be adapted to identify the location of the device 200A or 200B within the patient, for example, the location of a portion of the device 200A located between the first electrode and the second electrode.

In an example, where the circuit provides the signal based on impedance between the first electrode and the second electrode, a sinusoidal voltage can be applied between the first electrode and the second electrode. The sinusoidal voltage can be applied at a first frequency. Based on a relationship between the sinusoidal voltage and current between the first electrode and the second electrode, in terms of magnitude and relative phase, the circuit 124 can provide a signal based on the impedance between the first electrode and the second electrode.

In an example, the sinusoidal voltage can be applied at two excitation frequencies, such as 30 kHz and 50 MHz. The two excitation frequencies can be applied simultaneously or sequentially. Accordingly, increased discrimination between the electrical characteristic of a first tissue and the electrical characteristic of a second tissue can be achieved. For instance, as shown in the example of FIGS. 3A-B, the permittivity and conductivity can vary as a function of frequency. In a further example, the sinusoidal voltage having a broad spectrum signal, such as white noise, can be applied in order to excite many frequencies at once. Accordingly, the circuit 124 can simultaneously provide one or more signals based on a plurality of excitation frequencies.

FIG. 4 is a perspective view of a device 200C. In the example of FIG. 4, a detailed partial view of the device 200C is shown to better illustrate the detail of the device 200C. Accordingly, the entire length of the device 200C is not illustrated or drawn to scale. The device 200C can include the polymer needle 102A or 102B as previously described. In the example of FIG. 4, the device 200C includes the polymer needle 102A. The polymer needle 102A can be located within the elongate sleeve 104A or 104B. In the example of FIG. 4, the device 200C includes the elongate sleeve 104A. An insulated covering 400 can be located on the elongate sleeve 104A. For instance, the insulated covering 400 can be attached to an outer surface 402 of the elongate sleeve 104A. The insulated covering 400 can include a dielectric material to electrically isolate the user from the first electrode and the second electrode, such as the elongate sleeve 104A or the stylet 218. In various examples, the insulated covering 400 can include an epoxy, a polymer, an elastomer, or other dielectric material. The insulated covering 400 can be fixedly attached to the outer surface 402 of the elongate sleeve 104A so the insulated covering 400 does not slide with respect to the elongate sleeve 104A. In one example, the insulated covering 400 can include a textured surface to increase grip.

Figure 5:
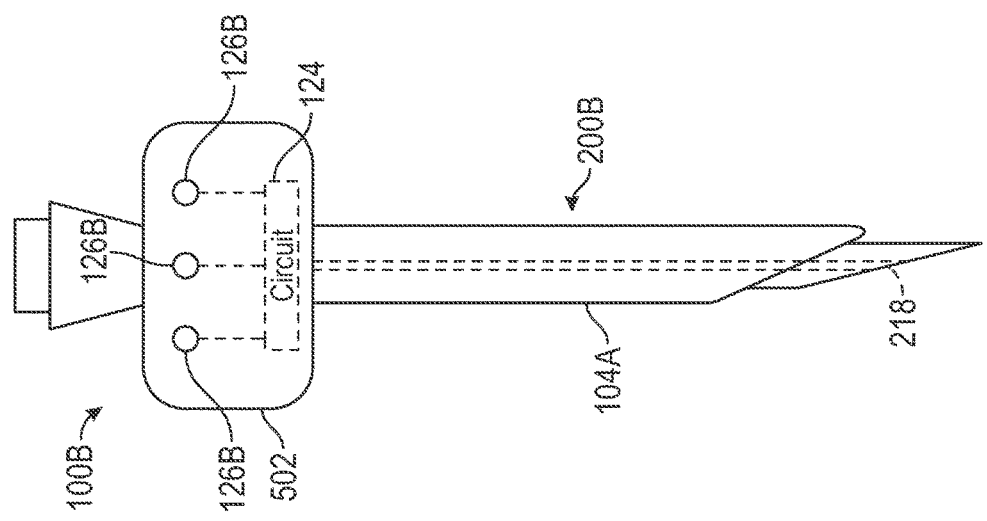
FIG. 5 depicts an example of a device including one or more indicators, according to an embodiment.

FIG. 5 depicts an example of a detection system 100B including an indicator 126B. In the example of FIG. 5, the detection system 100B includes a plurality of indicators 126B located within a housing 502. The device 200B can also be coupled to the housing 502. In an example, the housing 502 can include the circuit 124. The circuit 124 can be electrically coupled to the first electrode and the second electrode. In the example of FIG. 5, the stylet 218 is the first electrode and the elongate sleeve 104A is the second electrode. The circuit 124 can also be electrically coupled to the at least one indicator 126B. At least one of the indicators 126B can provide an output based on the signal. In the example of FIG. 5, the signal can correspond to the electrical characteristic between the stylet 218 and the elongate sleeve 104A. In an example, two or more indicators 126B, or each of the indicator 126B, can provide a respective output based on a plurality of respective signals from the circuit 124. For instance, in the example of FIG. 5, the indicator 126B can include at least one light emitting diode (LED). The LED can illuminate to provide the output. The illumination can correspond to at least one signal. In various examples, the output can include illuminating the LED having a color. For instance, the LED can emit a color including, but not limited to, red, blue, yellow, green, purple, orange, or other color. One or more respective LEDs can emit a different color than one or more other LEDs. In one example, each LED can emit a different color than the other LEDs. The color can correspond to a tissue or fluid located between the first electrode and the second electrode. In a further example, the detection system 100B, the device 200B, or both can be disposable to increase sanitation or to reduce administrative costs associated with tracking and maintaining capital equipment. The device 200B can be removably attached to the housing 502 and the circuit 124 to replace the device 200B, circuit 124, indicator 126B, or other component. In the example of FIG. 5 the entire length of the device 200B is not illustrated or drawn to scale.

Figure 6:
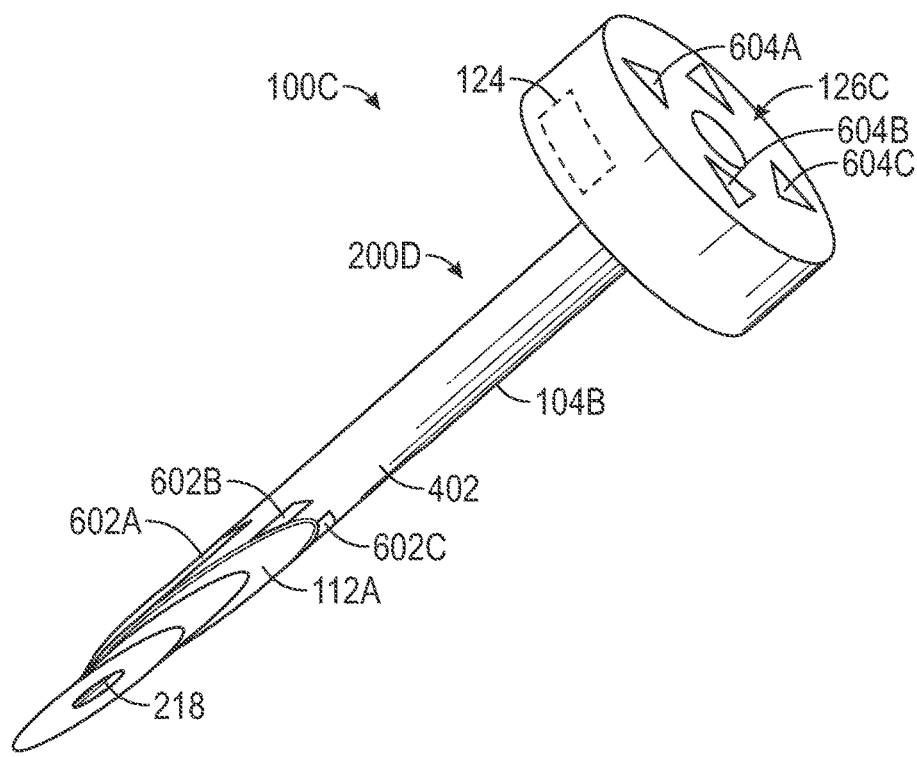
FIG. 6 is a perspective view of an example of a detector including a plurality of second electrodes located on different sides of a device, according to an embodiment.

FIG. 6 shows an example of a detection system 100C including a plurality of second electrodes, such as 602A, 602B, or 602C. In the example of FIG. 6, the entire length of the device 200D is not illustrated or drawn to scale to better illustrate the detail of the device 200D. In other examples, the detection system 100C can include at least two second electrodes. For instance, the detection system 100C can include two, ten, or any number of second electrodes in between. At least one second electrode, such as 602A, 602B, or 602C can be electrically isolated from one other second electrode 602A, 602B, or 602C. In an example, each of the second electrodes 602A, 602B, or 602C can be electrically isolated form one another. In the example of FIG. 6, the stylet 218 can be the first electrode. At least one second electrode 602A, 602B, or 602C can be located on a different side of the device 200D than at least one other second electrode 602A, 602B, or 602C. In one example, each second electrode 602A, 602B, or 602C can be located on a different respective side of the device 200D. For instance, the second electrodes 602A, 602B, or 602C can be located on the outer surface 402 of the elongate sleeve 104B. In the example of FIG. 6, the second electrodes 602A, 602B, or 602C can be located adjacent to the first end 112A. In some examples, the second electrodes 602A, 602B, or 602C can be radially arranged around the outer surface 402 of the elongate sleeve 104B as shown in FIG. 6.

In an example, the detection system 100C can include a plurality of indicators 126C. As shown in FIG. 6, the indicator 126C include, directional indicators, such as directional indicators 604A, 604B, or 604C. In other examples, the indicator 126C can include between two and ten directional indicators. In a further example, the indicator 126C can include a display configured to show directional indicators, such as 604A, 604B, or 604C. The display can be located on the device 200B, or the device 200B can be communicatively coupled to a computer or other remote display including the indicator 126C. At least one of the directional indicators 604A, 604B, or 604C can correspond to a respective side of the detection system 100C. For instance, the directional indicator 604A can be configured to receive the signal from the circuit 124 based on the electrical characteristic between the first electrode, e.g., stylet 218, and the second electrode 602A. Where the electrical characteristics between the first electrode and the second electrode 602A are within a target range, the circuit 124 can send the signal to the direction indicator 604A. The directional indicator 604A can then provide an output, such as illuminating the directional indicator 604A. Accordingly, the detection system 100C can provide output indicating at least one side of the device 200D that is in contact with the target tissue or fluid, for instance, CSF, bone, ligament, fat, or other tissue of fluid.

Figure 7:
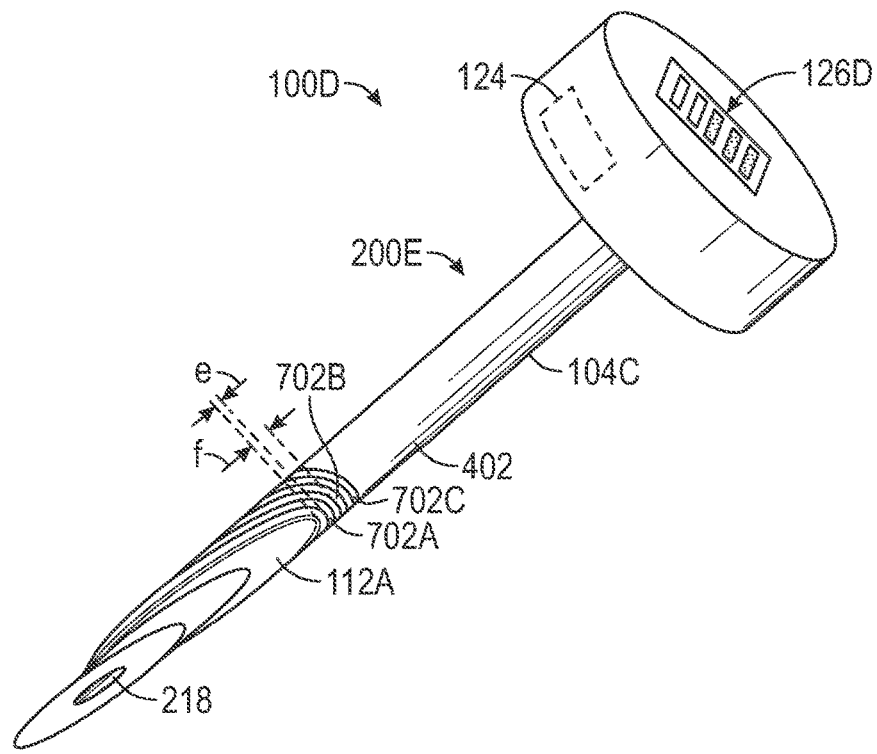
FIG. 7 is a perspective view of an example of a detector including a plurality of second electrodes positioned along a length of a device, according to an embodiment.

FIG. 7 illustrates an example of a detection system 100D including a plurality of second electrodes, such as second electrodes 702A, 702B, or 702C positioned along a length of the device 200E. For instance, the second electrode 702A can be located adjacent to the first end 112A. In the example of FIG. 7, the entire length of the device 200E is not illustrated or drawn to scale to better illustrate the detail of the device 200E. The second electrode 702B can be located at a first distance e from the first end 112A, and the second electrode 702C can be located at a second distance f from the first end 112A. In the example of FIG. 7, the second electrodes 702A, 702B, or 702C can be located on the outer surface 402 or an elongate sleeve 104C. At least one of the second electrodes 702A, 702B, or 702C can be electrically isolated from one other second electrodes 702A, 702B, or 702C. Accordingly, the output of an indicator 126D can show how deep the first electrode, such as the stylet 218, is located within the tissue. For instance, the circuit 124 can be configured to provide the signal based on the number of second electrodes, such as 702A, 702B, or 702C, that are in contact with the target tissue. In an example, the circuit 124 can be configured to provide the signal based on the electrical characteristic and the distance between the first electrode and the second electrode 702A, 702B, or 702C. In some examples, the second electrodes 702A, 702B, or 702C can be arranged axially along the outer surface 402 of the elongate sleeve 104C as shown in FIG. 7.

Figure 8:
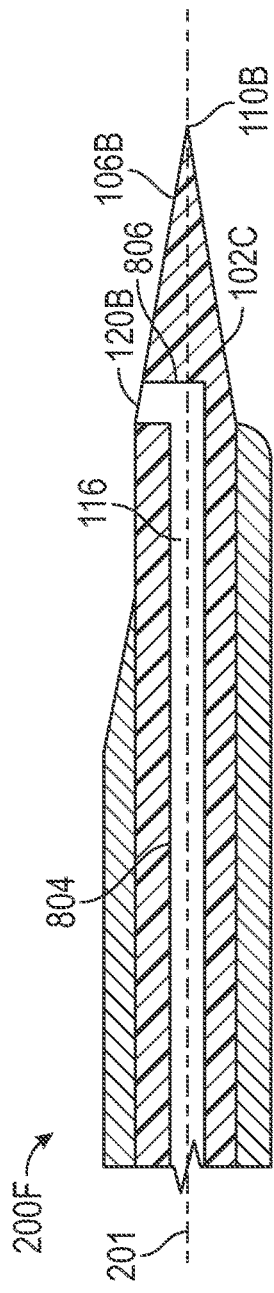
FIG. 8 is a cross section of a device including a polymer needle having a distal end with a pencil configuration, according to an embodiment.
Figure 9:
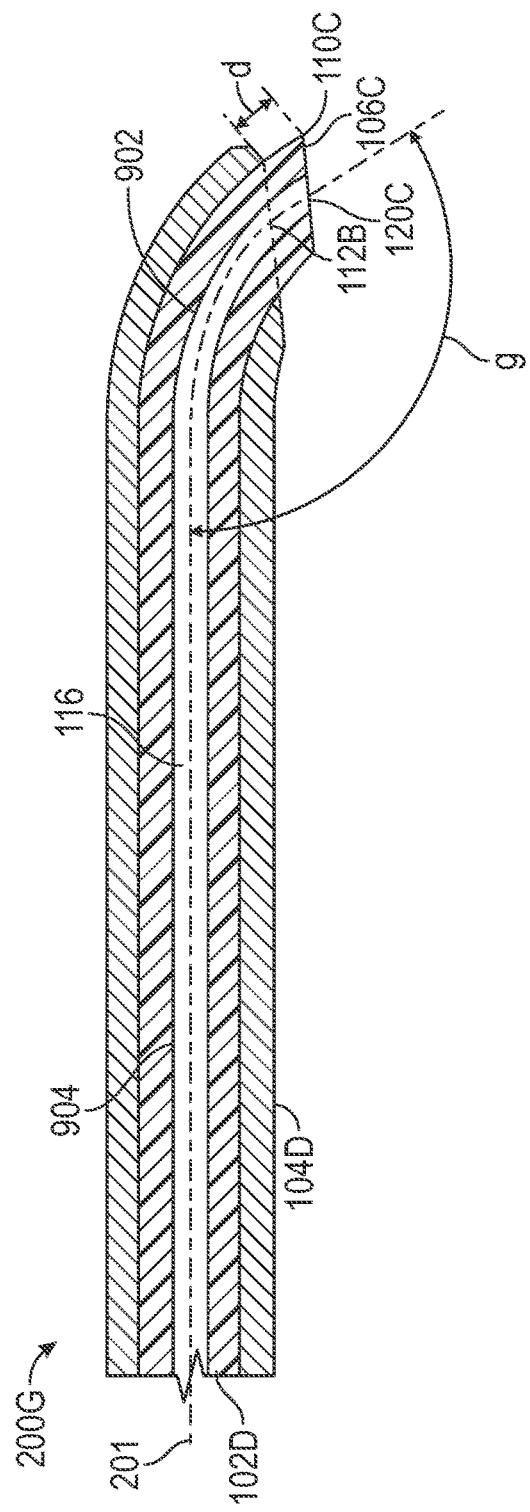
FIG. 9 is a cross section of a device including a polymer needle having a distal end with a Tuohy configuration, according to an embodiment.
Figure 10:
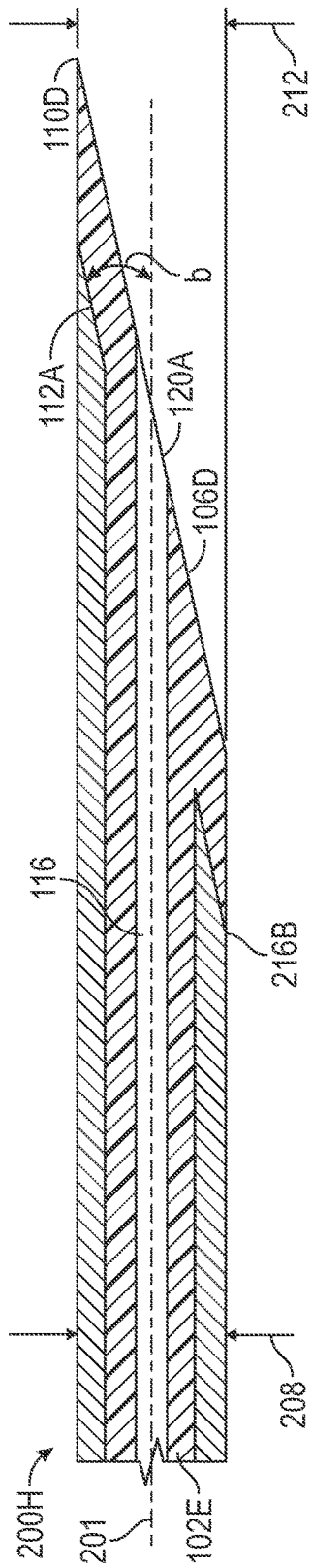
FIG. 10 is a cross section of a device including a polymer needle having a distal end having an outer dimension equal to an outer dimension of an elongate sleeve, according to an embodiment.

FIGS. 8-10 depict various examples of the device 200F, 200G, and 200H. Any of the devices 200F, 200G, or 200H can be included in the detection system 100A, 100B, 100C, or 100D. In the examples of FIGS. 8-10, the entire length of the devices 200F-H are not illustrated or drawn to scale to better illustrate the detail of the devices 200F-H. In various examples, the devices 200F, 200G, and 200H can include the stylet 218. In various examples, the stylet 218 can be the first electrode and the electrode pad 138 can be the second electrode, the stylet 218 can be the first electrode and the elongate sleeve 104A can be the second electrode, the elongate sleeve 104A can be the first electrode and the electrode pad 138 can be the second electrode, or the stylet 218 can be the first electrode and the devices 200F, 200G, or 200H can include the second electrodes, such as second electrodes 602A, 602B, 602C, 702A, 702B, or 702C.

FIG. 8 depicts an example of a cross section, along the longitudinal axis 201, of a device 200F including a polymer needle 102C. The polymer needle 102C can include a distal end 106B having a pencil configuration. The pencil configuration can include a convex, conical, or other shape profile, and have an insertion tip 110B for separating tissue. In the example of FIG. 8, the pencil configuration includes a tapered distal end 106B. An aperture 120B of the needle lumen 116 can be located on a lateral side of the distal end 106B. For instance, the needle lumen 116 can include an arcuate path. As shown in the example of FIG. 8, the needle lumen 116 includes a longitudinally oriented segment 804 and a laterally oriented segment 806. The laterally oriented segment 806 can terminate at the aperture 120B on the lateral side of the distal end 106B. Accordingly, the aperture 120B reduces discontinuity of the shape of the distal end 106B. For instance, the insertion tip 110B can be located on the longitudinal axis 201 (e.g., along a centerline of the distal end 106B).

FIG. 9 depicts an example of a cross section, along the longitudinal axis 201, of a device 200G including a polymer needle 102D. The polymer needle 102D can include a distal end 106C having a Tuohy needle configuration. In the example of FIG. 9, the distal end of the polymer needle 102D can include an arcuate shape. The device 200G can include an elongate sleeve 104D. The elongate sleeve 104D can include a first end 112B having an arcuate shape. For instance, a profile of the distal end 106C can follow a profile of the first end 112B. The distal end 106C is extended from the first end 112B by a distance d. As previously discussed, the polymer needle, such as polymer needle 102D, can include the lumen 116. In the example of FIG. 9, where the distal end 106C includes the Tuohy configuration, the lumen 116 can include a longitudinally oriented segment 904 extended along a longitudinal axis 201. The lumen 116 can terminate at an aperture 120C at the distal end 106C. The lumen 116 can include an arcuate segment 902 fluidly coupled between the aperture 120C and the longitudinal section 904. An orientation of the lumen 116 at the location of the aperture 120C can be aligned at an angle g with respect to the longitudinal axis 201. In various examples, the angle g can include an angle greater than 90 and less than 180 degrees. In one example, the angle g can include an angle between 110 and 130 degrees as shown in the example of FIG. 9. The distal end 106C can be tapered. For instance, the distal end 106C is tapered along the insertion direction of the device 200G.

FIG. 10 depicts an example of a cross section, along the longitudinal axis 201, of a device 200H including a polymer needle 102E. The polymer needle 102E can include a distal end 106D having an outer dimension 212 equal to or greater than the outer dimension 208. As shown in the example of FIG. 10, the outer dimension 212 is equal to the outer dimension 208. Accordingly, an insertion tip 110D can be located at the outer dimension 212 of the polymer needle 102E. In the example of FIG. 10, the dull transition 216B can include a flush interface between the outer dimension 208 and the outer dimension 212. The distal end 106D can cover the first end 112A. The first end 112A can be beveled as shown in the example of FIG. 10. In an example, the first end 112A can be aligned at the acute angle b. In a further example, the first end 112A can be oriented normal to the longitudinal axis 201. The polymer needle 102E can include the lumen 116 extended along the longitudinal axis 201 as previously described. The aperture 120A can be located at the distal end 106D at a location wherein the lumen 116 terminates.

Figure 11:
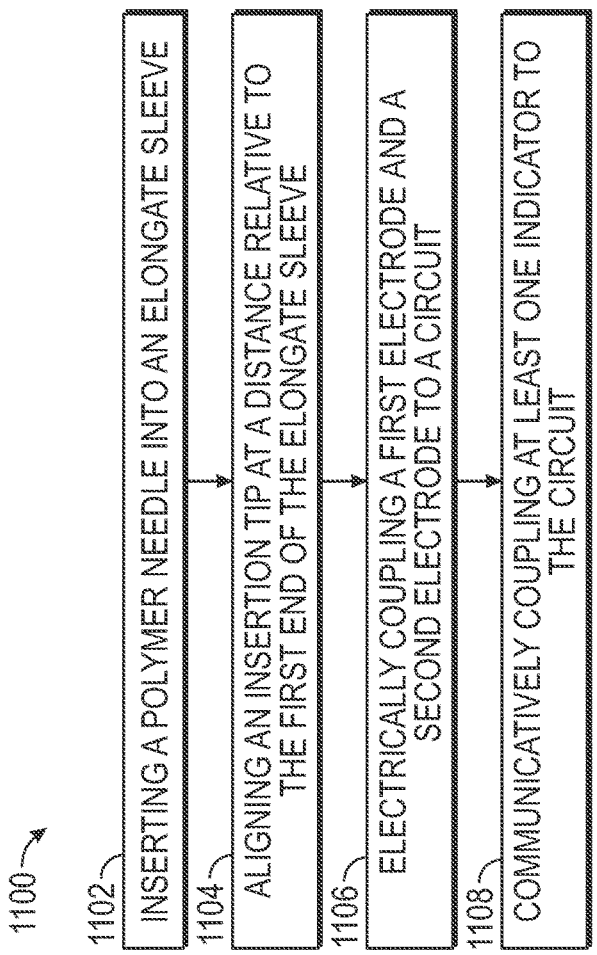
FIG. 11 is block diagram of an example of a method for making a device including a polymer needle, according to an embodiment.

FIG. 11 is a block diagram of one example of a method 1100 of constructing a detection system, such as 100A, 100B, 100C, or 100D previously described in the examples herein and shown, for instance, in FIGS. 1-10. In describing the method 1100, reference is made to one or more components, features, functions, or operations previously described herein. Where convenient, reference is made to the components, features, operations and the like with reference numerals. Reference numerals provided are examples and are nonexclusive. For instance, features, components, functions, operations, and the like described in the method 1100 include, but are not limited to, the corresponding numbered elements provided herein. Other corresponding features described herein (both numbered and unnumbered) as well as their equivalents are also considered.

At 1102, the polymer needle, such as 102A, 102B, 102C, 102D, or 102E can be inserted into the elongate sleeve 104A. In an example, the insulated covering 400 can be attached to the elongate sleeve 104A.

At 1104, the distal end 106 can be aligned at the distance d from the first end 112A. The distal end 106 can be aligned (e.g., translated) to a location where the distal end 106 is disposed at a distance d from the elongate sleeve 104A. For instance, the polymer needle 102B can be inserted into the elongate sleeve 104A and the polymer needle 102B and the elongate sleeve 104A can be cut at the acute angle b with respect to the longitudinal axis 201. Subsequently, the polymer needle 102B can be translated within the elongate sleeve 104A so the distal end 106 is located at the distance d from the first end 112A, as shown in FIG. 2 and described herein. The polymer needle, such as 102B can be constructed from a material including, but not limited to, PEEK, polytetrafluaroethlene (PTFE), polyethersulfone (PES), polysulfone (PS), polypropylene (PP), or other polymer. In a further example, the first end 112A can be shaped to include the dull transition 216 between the elongate sleeve 104A and the polymer needle 102B. In an example, an adhesive can be disposed between the polymer needle 102B and the elongate sleeve 104A to fixedly couple the polymer needle 102B to the elongate sleeve 104A. In a further example, the polymer needle 102B can be ultrasonically welded or press fit into the elongate sleeve 104A. In an example, the insertion tip 110A can be aligned at the distance d from the first end 112A of the elongate sleeve 104A. The length of the electrical path 230, such as a path of least electrical resistance or least electrical impedance, can be configured for detecting CSF, ligament tissue, or fatty tissue. For instance, the length of the electrical path 230 or distance between the first electrode and the second electrode, can be calibrated for the circuit 124 to provide the signal based on the electrical characteristic of a specific tissue. In an example, the distal stylet end 220 can be positioned laterally from the first end 112 to reduce the length of the electrical path 230. In an example, the length of the electrical path 230 can include, but is not limited to, between 0.1 mm and 1.0 mm. In an example, the length of the electrical path 230 can be 0.27 mm.

At 1106, the first electrode and the second electrode can be electrically coupled to the circuit 124. In an example, a plurality of second electrodes, such as 602A, 602B, or 602C can be electrically coupled to the circuit 124. The plurality of second electrodes 602A, 602B, or 602C can be electrically isolated from one another, and the first electrode can be electrically isolated from the one or more second electrodes. For instance, the polymer needle 102A can be arranged to electrically isolate the first electrode and the one or more second electrodes. In an example, the circuit 124 can be configured to provide the signal based on electrical impedance, for instance, an electrical impedance between the first electrode and the second electrode.

The first electrode and the at least one second electrode can be coupled to the device 200D. In an example, the plurality of second electrodes 602A, 602B, or 602C can be arranged on different respective sides of the device 200D or 200E. At least one indicator, such as indicator 126A, 126B, 126C, or directional indicator, such as 604A, 604B, or 604C can be configured to illuminate based on an electrical signal from one of the second electrodes. The indicator, such as 126A, 126B, 126C, or directional indicators, such as 604A, 604B, or 604C can correspond to one respective side of the device 200D.

At 1108, the at least one indicator, such as 126A, 126B, 126C, 126D, or directional indicator, such as 604A, 604B, or 604C can be communicatively coupled to the circuit 124. For instance, the indicator, such as indicator 126B can include one or more LEDs. In other examples, other indicators, such as the display, light, speaker, vibration motor, or other indicator can be communicatively coupled to the circuit 124. The plurality of indicators 126A, 126B, 126C, or 126D can be communicatively coupled to the circuit 124. In an example, the plurality of indicators 126A, 126B, 126C, 126D can be configured to provide the plurality of respective outputs based on the plurality of respective signals. In an example, the circuit 124 can be configured to provide the plurality of signals based on respective electrical characteristics corresponding to cerebral spinal fluid, ligament tissue, or fatty tissue.

VARIOUS NOTES & EXAMPLES

Each of these non-limiting examples may stand on its own, or may be combined in various permutations or combinations with one or more of the other examples. To better illustrate the method and apparatuses disclosed herein, a non-limiting list of embodiments is provided here:

Example 1 is a device comprising: a polymer needle including a distal end and a proximal end, wherein a needle lumen is extended along a longitudinal axis of the polymer needle, and wherein the distal end includes an insertion tip; and an elongate sleeve including a first end and a second end, wherein the polymer needle is fixedly attached to the elongate sleeve and located within an inner bore of the elongate sleeve, and the insertion tip of the polymer needle is disposed at a distance from the first end.

In Example 2, the subject matter of Example 1 optionally includes wherein the polymer needle includes polyether ether ketone (PEEK).

In Example 3, the subject matter of any one or more of Examples 1-2 optionally include wherein the distal end includes a pencil configuration and the needle lumen includes an aperture along a lateral side of the polymer needle.

In Example 4, the subject matter of any one or more of Examples 1-3 optionally include wherein the distal end includes a beveled configuration.

In Example 5, the subject matter of any one or more of Examples 1-4 optionally include wherein the first end of the elongate sleeve of includes a dull transition between an outer dimension and the inner bore of the elongate sleeve.

In Example 6, the subject matter of any one or more of Examples 1-5 optionally include a stylet located within the needle lumen including a proximal stylet end and a distal stylet end, wherein the distal stylet end is substantially aligned with an aperture of the needle lumen located on a surface of the distal end.

In Example 7, the subject matter of Example 6 optionally includes wherein the stylet includes a stylet lumen extended between the proximal stylet end and the distal stylet end.

In Example 8, the subject matter of any one or more of Examples 1-7 optionally include wherein the elongate sleeve includes an outer dimension between 0.2 mm to 4.5 mm, and the insertion tip of the polymer needle is disposed from the first end of the elongate sleeve at a distance between 0.1 mm and 10.0 mm.

Example 9 is a device comprising: a polymer needle including a distal end, a proximal end, and outer diameter, wherein a needle lumen is extended along a longitudinal axis of the polymer needle, and wherein the distal end includes an insertion tip having a beveled configuration; and an elongate sleeve including a first end and a second end, wherein the polymer needle is located within an inner bore of the elongate sleeve, and the insertion tip of the polymer needle is disposed from the elongate sleeve at a distance.

In Example 10, the subject matter of Example 9 optionally includes wherein the polymer needle includes polyether ether ketone (PEEK).

In Example 11, the subject matter of any one or more of Examples 9-10 optionally include wherein the needle lumen includes an aperture along a lateral side of the polymer needle.

In Example 12, the subject matter of any one or more of Examples 9-11 optionally include wherein a beveled surface of the distal end of the polymer needle and the first end of the elongate sleeve are aligned at an acute angle with respect to the longitudinal axis of the polymer needle and a beveled surface of the distal end is disposed from the first end of the elongate sleeve at the distance.

In Example 13, the subject matter of any one or more of Examples 9-12 optionally include wherein the first end of the elongate sleeve includes a dull transition between an inner bore and an outer dimension of the elongate sleeve.

In Example 14, the subject matter of any one or more of Examples 9-13 optionally include a stylet located within the needle lumen including a proximal stylet end and a distal stylet end, wherein the distal stylet end is substantially aligned with an aperture of the needle lumen located on the distal end.

In Example 15, the subject matter of Example 14 optionally includes wherein the stylet includes a stylet lumen extended between the proximal stylet end and the distal stylet end.

In Example 16, the subject matter of any one or more of Examples 9-15 optionally include wherein the elongate sleeve includes an outer dimension between 0.2 mm to 4.5 mm, and a ratio of the distance to the outer dimension is between 0.02 and 50.

Example 17 is a method comprising: inserting a polymer needle into an elongate sleeve, wherein: the polymer needle includes a proximal end, a distal end having an insertion tip, and a needle lumen extended along a longitudinal axis of the polymer needle, the needle lumen includes an aperture at the distal end, the elongate sleeve includes a first end and a second end, wherein the polymer needle is located within an inner bore of the elongate sleeve; and aligning the insertion tip at a distance from the first end of the elongate sleeve, wherein the insertion tip is disposed from the sleeve.

In Example 18, the subject matter of Example 17 optionally includes locating a stylet within the needle lumen, wherein the stylet includes a proximal stylet end and a distal stylet end, and the distal stylet end is substantially aligned with the aperture of the polymer needle.

In Example 19, the subject matter of any one or more of Examples 17-18 optionally include wherein inserting the polymer needle into the elongate sleeve, includes inserting the polymer needle including a polyether ether ketone (PEEK) material.

In Example 20, the subject matter of any one or more of Examples 17-19 optionally include wherein inserting the polymer needle into the elongate sleeve, includes inserting the polymer needle wherein the distal end of the polymer needle includes a pencil configuration and the needle lumen includes an aperture along a surface of the distal end.

In Example 21, the subject matter of any one or more of Examples 17-20 optionally include wherein inserting the polymer needle into the elongate sleeve, includes inserting the polymer needle wherein the distal end of the polymer needle includes a beveled configuration.

In Example 22, the subject matter of any one or more of Examples 17-21 optionally include wherein inserting the polymer needle into the elongate sleeve, includes the elongate sleeve having a dull transition at the first sleeve end between an outer dimension and the inner bore of the elongate sleeve.

In Example 23, the subject matter of any one or more of Examples 17-22 optionally include wherein inserting the polymer needle into the elongate sleeve, includes inserting the polymer needle into the elongate sleeve including an outer dimension between 0.2 mm to 4.5 mm, and a ratio of the distance to the outer dimension is between 0.02 and 50.

Example 24 is a detection system comprising: a device including a polymer needle and an elongate sleeve wherein, the polymer needle includes a distal end and a proximal end, wherein a needle lumen is extended along a longitudinal axis of the polymer needle, and wherein the distal end includes an insertion tip; the elongate sleeve includes a first end and a second end, wherein the polymer needle is located within an inner bore of the elongate sleeve, and the insertion tip of the polymer needle is disposed at a distance from the elongate sleeve; a first electrode coupled to the device; a second electrode electrically isolated from the first electrode; a circuit configured to provide a signal based on an electrical characteristic between the first electrode and the second electrode; and at least one indicia communicatively coupled to the circuit and configured to provide an output based on the signal.

In Example 25, the subject matter of Example 24 optionally includes wherein the signal is based on an electrical characteristic of cerebral spinal fluid.

In Example 26, the subject matter of any one or more of Examples 24-25 optionally include a plurality of indicia, wherein the plurality of indicia provide a respective output based on a plurality of respective signals.

In Example 27, the subject matter of Example 26 optionally includes where the respective electrical characteristics are based on at least cerebral spinal fluid, ligament, and fat.

In Example 28, the subject matter of any one or more of Examples 24-27 optionally include a plurality of second electrodes, wherein the plurality of second electrodes are electrically isolated from one another.

In Example 29, the subject matter of Example 28 optionally includes wherein the device includes two or more sides and the plurality of second electrodes are arranged on different respective sides of the device.

In Example 30, the subject matter of Example 29 optionally includes wherein the at least one indicia is configured to illuminate based on an electrical signal from one of the second electrodes, wherein the at least one indicia corresponds to one respective side of the device.

In Example 31, the subject matter of any one or more of Examples 24-30 optionally include wherein the elongate sleeve includes an insulated covering.

In Example 32, the subject matter of any one or more of Examples 24-31 optionally include wherein a length of a path of least electrical resistance between the first electrode and the second electrode is configured for detecting cerebral spinal fluid.

In Example 33, the subject matter of any one or more of Examples 24-32 optionally include wherein, a ratio of the distance to an outer sleeve dimension is between 0.02 and 50, and the ratio is configured for detecting cerebral spinal fluid.

In Example 34, the subject matter of any one or more of Examples 24-33 optionally include wherein the electrical characteristic is impedance.

In Example 35, the subject matter of any one or more of Examples 24-34 optionally include wherein the output is provided based on the signal corresponding to the electrical characteristic being within a target range.

In Example 36, the subject matter of any one or more of Examples 24-35 optionally include wherein the elongate sleeve is the first electrode and an electrode pad is the second electrode, wherein the electrode pad is configured for placement on skin of a patient.

In Example 37, the subject matter of any one or more of Examples 24-36 optionally include a stylet located within the needle lumen, the stylet including a proximal stylet end and a distal stylet end, wherein the distal stylet end is located at the distal end.

In Example 38, the subject matter of Example 37 optionally includes wherein the stylet is the first electrode and an electrode pad is the second electrode, wherein the electrode pad is configured for placement on skin of a patient.

In Example 39, the subject matter of any one or more of Examples 37-38 optionally include wherein the stylet is the first electrode and the elongate sleeve is the second electrode.

In Example 40, the subject matter of any one or more of Examples 24-39 optionally include wherein the indicia is an LED configured to illuminate based on the output.

Example 41 is a detection system comprising: a device including a polymer needle, a stylet, and an elongate sleeve wherein, the polymer needle includes a distal end and a proximal end, wherein a needle lumen is extended along a longitudinal axis of the polymer needle, and wherein the distal end includes an insertion tip; the stylet is located within the needle lumen and adapted as a first electrode, the stylet including a proximal stylet end and a distal stylet end, wherein the distal stylet end is located at the distal end the elongate sleeve includes a first end and a second end, wherein the polymer needle is located within an inner bore of the elongate sleeve, and the insertion tip of the polymer needle is disposed at a distance from the elongate sleeve, and wherein the elongate sleeve is adapted as a second electrode isolated from the first electrode by the polymer needle; a circuit configured to provide a signal based on an electrical characteristic between the stylet and the elongate sleeve; and at least one indicia communicatively coupled to the circuit and configured to provide an output based on the signal.

In Example 42, the subject matter of any one or more of Examples 24-41 optionally include wherein the signal is based on an electrical characteristic of cerebral spinal fluid.

In Example 43, the subject matter of any one or more of Examples 24-42 optionally include a plurality of indicia providing a plurality of respective outputs based on a plurality of respective electrical characteristics.

In Example 44, the subject matter of Example 43 optionally includes where the respective electrical characteristics are based on at least cerebral spinal fluid, ligament, and fat.

In Example 45, the subject matter of any one or more of Examples 24-44 optionally include wherein the elongate sleeve includes an insulated covering.

In Example 46, the subject matter of any one or more of Examples 24-45 optionally include wherein a length of a path of least electrical resistance between the first electrode and the second electrode is configured for detecting cerebral spinal fluid.

In Example 47, the subject matter of any one or more of Examples 24-46 optionally include wherein, a ratio of the distance to an outer sleeve dimension is between 0.02 and 50, and the ratio is configured for detecting cerebral spinal fluid.

In Example 48, the subject matter of any one or more of Examples 24-47 optionally include wherein the electrical characteristic is impedance.

In Example 49, the subject matter of any one or more of Examples 24-48 optionally include wherein the output is provided based on the signal corresponding to the electrical characteristic being within a target range.

In Example 50, the subject matter of any one or more of Examples 24-49 optionally include wherein the indicia is an LED configured to illuminate based on the output.

In Example 51, the subject matter of any one or more of Examples 32-50 optionally include wherein the polymer needle includes polyether ether ketone (PEEK).

In Example 52, the subject matter of any one or more of Examples 24-51 optionally include wherein the distal end includes a beveled configuration.

Example 53 is a method comprising: inserting a polymer needle into an elongate sleeve, wherein: the polymer needle includes a proximal end, a distal end having an insertion tip, and a needle lumen extended along a longitudinal axis of the polymer needle, the needle lumen includes an aperture at the distal end, the elongate sleeve includes a first end and a second end, wherein the polymer needle is located within an inner bore of the elongate sleeve; and aligning the insertion tip at a distance from the first end of the elongate sleeve, wherein the insertion tip is disposed from the sleeve; electrically coupling a first electrode and a second electrode to a circuit, wherein the first electrode is electrically isolated from the second electrode, and the circuit is configured to provide a signal based on an electrical characteristic between the first electrode and the second electrode; and communicatively coupling at least one indicia to the circuit, wherein the indicia is configured to provide an output based on the signal.

In Example 54, the subject matter of Example 53 optionally includes wherein electrically coupling the first electrode and the second electrode to the circuit includes configuring the circuit to provide the signal based on an electrical characteristic of cerebral spinal fluid.

In Example 55, the subject matter of any one or more of Examples 53-54 optionally include wherein communicatively coupling at least one indicia to the circuit further comprises communicatively coupling a plurality of indicia to the circuit, the plurality of indicia configured to provide a plurality of respective outputs based on a plurality of respective signals.

In Example 56, the subject matter of Example 55 optionally includes wherein communicatively coupling the plurality of indicia to the circuit further comprises configuring the circuit to provide a plurality of signals based on respective electrical characteristics corresponding to cerebral spinal fluid, ligament tissue, and fatty tissue.

In Example 57, the subject matter of any one or more of Examples 53-56 optionally include wherein electrically coupling the first electrode and the second electrode to the circuit further comprises electrically coupling a plurality of second electrodes to the circuit, wherein the plurality of second electrodes are electrically isolated from one another.

In Example 58, the subject matter of Example 57 optionally includes wherein the device includes two or more sides and the plurality of second electrodes are arranged on different respective sides of the device.

In Example 59, the subject matter of Example 58 optionally includes wherein the at least one indicia is configured to illuminate based on an electrical signal from one of the second electrodes, wherein the at least one indicia corresponds to one respective side of the device.

In Example 60, the subject matter of any one or more of Examples 53-59 optionally include wherein inserting the polymer needle into the elongate sleeve includes inserting the polymer needle into the elongate sleeve including an insulated covering.

In Example 61, the subject matter of any one or more of Examples 53-60 optionally include wherein aligning the insertion tip at the distance from the first end of the elongate sleeve includes aligning the insertion tip at a distance from the first end where a length of a path of least electrical resistance between the first electrode and the second electrode is configured for detecting cerebral spinal fluid.

In Example 62, the subject matter of any one or more of Examples 53-61 optionally include wherein inserting the polymer needle into the elongate sleeve includes inserting the polymer needle and the elongate sleeve wherein a ratio of the distance to an outer sleeve dimension is between 0.02 and 50.

In Example 63, the subject matter of any one or more of Examples 53-62 optionally include wherein electrically coupling the first electrode and the second electrode to the circuit further comprises configuring the circuit to provide the signal based on impedance.

In Example 64, the subject matter of any one or more of Examples 53-63 optionally include wherein communicatively coupling at least one indicia to the circuit includes providing the output based on the signal corresponding to the electrical characteristic being within a target range.

In Example 65, the subject matter of any one or more of Examples 53-64 optionally include wherein electrically coupling the first electrode and the second electrode to the circuit includes the elongate sleeve adapted as the first electrode and an electrode pad adapted as the second electrode, wherein the electrode pad is configured for placement on skin of a patient.

In Example 66, the subject matter of any one or more of Examples 53-65 optionally include removably inserting a stylet into the needle lumen, wherein, the stylet includes an elongate stylet shaft extended between a proximal stylet end and a distal stylet end.

In Example 67, the subject matter of Example 66 optionally includes wherein electrically coupling the first electrode and the second electrode to the circuit includes the stylet adapted as the first electrode and an electrode pad adapted as the second electrode, wherein the electrode pad is configured for placement on skin of a patient.

In Example 68, the subject matter of any one or more of Examples 66-67 optionally include wherein electrically coupling the first electrode and the second electrode to the circuit includes the stylet adapted as the first electrode and the elongate sleeve adapted as the second electrode.

In Example 69, the subject matter of any one or more of Examples 53-68 optionally include wherein communicatively coupling at least one indicia to the circuit includes communicatively coupling an LED configured to illuminate based on the output.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device for use in a tissue detection system, the device comprising:
   a polymer needle including a distal end and a proximal end, wherein a needle lumen is extended along a longitudinal axis of the polymer needle, and wherein the distal end includes an insertion tip;
   an elongate sleeve including a first end and a second end, wherein the polymer needle is fixedly attached to the elongate sleeve and located within an inner bore of the elongate sleeve, and the insertion tip of the polymer needle is disposed at a distance from the first end; and
   a stylet located within the needle lumen, the stylet configured as a first electrode for creating an electrical circuit with a second electrode electrically isolated from the stylet,
   wherein the electrical circuit provides a signal based on an electrical characteristic between the first and second electrodes.

2. The device of claim 1, wherein the distal end includes a beveled configuration.

3. The device of claim 1, wherein a beveled surface of the distal end of the polymer needle and the first end of the elongate sleeve are aligned at an acute angle with respect to the longitudinal axis of the polymer needle and the beveled surface of the distal end is disposed from the first end of the elongate sleeve at the distance.

4. The device of claim 1, wherein the distal end has an outer dimension normal to a longitudinal axis of the polymer needle that is equal to or greater than an outer dimension of the elongate sleeve normal to a longitudinal axis of the elongate sleeve.

5. The device of claim 1, wherein the polymer needle includes polyether ether ketone (PEEK).

6. The device of claim 1, wherein the first end of the elongate sleeve includes a dull transition between an outer dimension and the inner bore of the elongate sleeve.

7. The device of claim 1, wherein the stylet includes a proximal stylet end and a distal stylet end, wherein the distal stylet end is substantially aligned with an aperture of the needle lumen located on a surface of the distal end.

8. The device of claim 7, wherein the stylet includes a stylet lumen extended between the proximal stylet end and the distal stylet end.

9. The device of claim 1, wherein the elongate sleeve includes an outer dimension between 0.2 mm to 4.5 mm, and the insertion tip of the polymer needle is disposed from the first end of the elongate sleeve at a distance between 0.1 mm and 10.0 mm.

10. A detection system comprising:
    a device including a polymer needle and an elongate sleeve wherein,
    the polymer needle includes a distal end and a proximal end, wherein
    a needle lumen is extended along a longitudinal axis of the polymer needle, and wherein the distal end includes an insertion tip; and
    the elongate sleeve includes a first end and a second end, wherein the polymer needle is located within an inner bore of the elongate sleeve such that the needle lumen and elongate sleeve are coaxial, and the insertion tip of the polymer needle is disposed at a distance from the elongate sleeve;
    a first electrode coupled to the device;
    a second electrode electrically isolated from the first electrode;
    a circuit configured to provide a signal based on an electrical characteristic between the first electrode and the second electrode; and
    at least one indicator communicatively coupled to the circuit and configured to provide an output based on the signal.

11. The detection system of claim 10, wherein the electrical characteristic is impedance, and the output is provided based on the signal corresponding to the electrical characteristic being within a target range.

12. The detection system of claim 11, wherein the circuit is configured to provide the signal at a first sinusoidal voltage and at a second sinusoidal voltage, simultaneously or sequentially, between the first electrode and a second electrode to discriminate between a plurality of tissues based on the electrical characteristic.

13. The detection system of claim 11, wherein the circuit is configured to provide the signal between the first electrode and a second electrode at a broad spectrum of voltages simultaneously to discriminate between a plurality of tissues based on the electrical characteristic.

14. The detection system of claim 10, further comprising a stylet located within the needle lumen, the stylet including a proximal stylet end and a distal stylet end, wherein the distal stylet end is located at the distal end, and wherein the stylet is the first electrode and an electrode pad is the second electrode, wherein the electrode pad is configured for placement on skin of a patient.

15. The detection system of claim 10, further comprising a stylet located within the needle lumen, the stylet including a proximal stylet end and a distal stylet end, wherein the distal stylet end is located at the distal end, and wherein the stylet is the first electrode and the elongate sleeve is the second electrode.

16. The detection system of claim 15, wherein the elongate sleeve includes an insulated covering.

17. The detection system of claim 10, wherein the distal end includes a beveled configuration.

18. The detection system of claim 10, wherein the signal is based on an electrical characteristic of cerebral spinal fluid.

19. The detection system of claim 10, further comprising a plurality of indicators, wherein the plurality of indicators provide a respective output based on a plurality of respective signals.

20. The detection system of claim 10, wherein the second electrode is a plurality of second electrodes, wherein the plurality of second electrodes are electrically isolated from one another.

21. The detection system of claim 20, wherein the device includes two or more sides and the plurality of second electrodes are arranged on different respective sides of the device.

22. The detection system of claim 21, wherein the at least one indicator is configured to illuminate based on an electrical signal from one of the second electrodes, wherein the at least one indicator corresponds to one respective side of the device.

23. The detection system of claim 10, wherein the at least one indicator is an LED configured to illuminate based on the output.

24. A detection system comprising:
a device comprising:
a polymer needle having a needle lumen extending along a longitudinal axis of the device;
an elongate sleeve having an inner bore extending along the longitudinal axis, the polymer needle located within the inner bore; and
a stylet located within the needle lumen, the stylet configured as a first electrode;
a plurality of second electrodes on the device, the plurality of second electrodes electrically isolated from one another and the first electrode; and
a circuit configured to provide a signal based on an electrical characteristic between the first electrode and at least one of the plurality of second electrodes.

25. The detection system of claim 24, wherein the plurality of second electrodes are spaced apart from each other on an outer surface of the elongate sleeve.

26. The detection system of claim 25, wherein the plurality of second electrodes are arranged radially around the outer surface of the elongate sleeve.

* * * * *